(12) United States Patent
Sáyago (10) Patent No.: US 12,171,684 B2
(45) Date of Patent: Dec. 24, 2024

(54) APPARATUS FOR REDUCING CLOSED FRACTURES OF THE BONES OF THE FOREARM AND OF THE WRIST WITH A CLOSED TECHNIQUE

(71) Applicant: Rubén Fernando Sáyago, Navojoa (MX)

(72) Inventor: Rubén Fernando Sáyago, Navojoa (MX)

( * ) Notice: Subject to any disclaimer, the term of this patent is extended or adjusted under 35 U.S.C. 154(b) by 595 days.

(21) Appl. No.: 17/424,997

(22) PCT Filed: Nov. 14, 2019

(86) PCT No.: PCT/MX2019/050024
§ 371 (c)(1),
(2) Date: Jul. 22, 2021

(87) PCT Pub. No.: WO2020/162740
PCT Pub. Date: Aug. 13, 2020

(65) Prior Publication Data
US 2022/0087846 A1 Mar. 24, 2022

(30) Foreign Application Priority Data

Feb. 5, 2019 (MX) .................. MX/A/2019/001514

(51) Int. Cl.
*A61F 5/04* (2006.01)
*A61F 5/01* (2006.01)
*A61F 5/042* (2006.01)

(52) U.S. Cl.
CPC ................ *A61F 5/013* (2013.01); *A61F 5/04* (2013.01); *A61F 5/042* (2013.01); *A61F 2005/0155* (2013.01)

(58) Field of Classification Search
CPC .. A61F 5/013; A61F 5/04; A61F 5/042; A61F 2005/0155; A61H 1/02;
(Continued)

(56) References Cited

U.S. PATENT DOCUMENTS 2,053,632 A 9/1936 Putney
2,286,556 A 3/1940 Longfellow
(Continued)

FOREIGN PATENT DOCUMENTS

CN 106491196 A 3/2017
ES 1229902 U 5/2019
(Continued)

OTHER PUBLICATIONS

International Search Report of the ISA/ES in PCT/MX2019/050024, dated Mar. 11, 2020; 10pgs.

*Primary Examiner* — Keri J Nelson
(74) *Attorney, Agent, or Firm* — Haukaas Fortius PLLC; Paul K. Judd; Michael Haukaas (57) ABSTRACT

The present invention relates to a non-automated apparatus for manipulating and reducing closed fractures of the ulna and radius at the level of the wrist in children and adults, which consists of a bar (1) designed to be able to position the fractured limb on the bar, the other nine parts of the apparatus being custom assembled according to the measurement of the forearm or writ to be manipulated, enabling a single person to reduce the fracture using three phases or movements of the device. The design and materials from which the apparatus is made allow the mentioned fractures to be reduced and safety stops are provided to prevent any harm to the patient. The manipulation or reduction of the fractures on which the present apparatus is used must preferably be handled by a doctor specialised in traumatology and orthopaedics.

1 Claim, 7 Drawing Sheets

(58) Field of Classification Search
CPC .. A61H 1/0218; A61H 1/0274; A61H 1/0277; A61H 1/0281; A61H 1/0285
See application file for complete search history.

(56) References Cited

U.S. PATENT DOCUMENTS

| | | | | |
|---|---|---|---|---|
| 2,590,739 A * | 3/1952 | Wagner | ............... | A61F 5/04 D24/188 |
| 2,614,558 A | 10/1952 | Lovell | | |
| 4,669,451 A * | 6/1987 | Blauth | ............... | A61H 1/02 482/901 |
| 5,084,047 A * | 1/1992 | Naraghi | ............... | A61F 5/04 606/53 |
| 6,001,097 A * | 12/1999 | Campopiano | ......... | A61B 17/66 606/57 |
| 6,123,704 A * | 9/2000 | Hajianpour | ............ | A61F 5/04 606/54 |
| 7,131,955 B2 * | 11/2006 | Price | ............... | A61F 5/3761 602/20 |
| 8,690,808 B2 * | 4/2014 | Reiley | ............ | A61B 17/1739 602/23 |
| 9,757,267 B1 | 9/2017 | Ramazanian et al. | | |

FOREIGN PATENT DOCUMENTS

| | | | |
|---|---|---|---|
| GB | 466441 A | 5/1937 | |
| WO | 2011149932 A1 | 12/2011 | |

\* cited by examiner

APPARATUS FOR REDUCING CLOSED FRACTURES OF THE BONES OF THE FOREARM AND OF THE WRIST WITH A CLOSED TECHNIQUE

CROSS-REFERENCE TO RELATED APPLICATIONS

This application is a National Stage filing under 35 U.S.C. § 371 of International Application No. PCT/MX2019/050024, filed Nov. 14, 2019, which claims the benefit of Mexican Patent Application No. MX/a/2019/001514 filed Feb. 5, 2019, which applications are incorporated herein by reference.

TECHNICAL FIELD

This invention relates to an apparatus which purpose is to treat closed fractures without surgery (also known as closed technique) of the bones of the forearm (which name is ulna and radius) in children, and of wrist in children and adults, thus treating with this apparatus a problem faced by orthopaedic and orthopaedist surgeons due to the situations referred to hereinbelow but to really understand the invention of this apparatus, a definition of some medical terms will be provided in the first place:

Fractures are generally classified into open and closed fractures; open fractures are those in which there is a wound on the injury site and the fractured bone is exposed out of the skin and the closed fractures are those in which there is no exposition of the fractured bone out of the skin and there is generally no wound on the site of fracture and due to their location in the involved bones, they are diaphyseal when they are in the ⅓ half of its long and metaphyseal when they are in ⅓ of the ends; based on the above, this apparatus will only be useful in the metaphyseal fractures in children and adults and diaphyseal in children when the closed reduction is possible.

The way to treat such fractures is:

1. With surgery technique or open reduction, namely operating patient and reducing the fracture (reducing a fracture means arranging or aligning the bond as it was before the fracture) and fixing the fracture with a fixing system such as a screw plate, a nail, wire, external fixators or a combination of some of them.

2. With closed technique, without operating patient, consisting in the manipulation of the fracture for reducing it and the fixation may be with external fixators or with a plaster mold that will be worn by patient until consolidation of fracture.

In case of any open fracture, treatment thereof is 100% surgical but in closed fractures treatment may be with a surgical or open technique or with a closed technique without operating patient.

BACKGROUND OF THE INVENTION

Fractures of the forearm bones (denominated ulna and radius) and wrist bones (denominated ulna, radius and carpus) in humans are very frequent, in the case of children from 45% to 55% total fractures and from 60% to 65% total fractures of the thoracic member; and from 66% to 75% correspond to ⅓ distal of the forearm and only 20% of ⅓ half of the forearm, between the age of 4 to 12 years old and the reasons are obvious due to the nature of children that suddenly jump, play and run a lot and they frequently suffer falls, putting ahead their hands when they fall as a usual defense means thus causing the fracture.

In the case of adults older than 45 years old, wrist fractures also increase in frequency up to 25% of all fractures, women are 4 times more affected than men in this type of fractures; reason are due to falls from their own height and putting ahead their hand as a usual defense instinct.

Treatment of forearm closed fractures in children is conservative in 70% of the cases by means of treatment with anesthesia with the traditional technique, with the elbow at 90 degrees flexion and making longitudinal traction (in the axis) in the fractured bone and counter traction in the arm until achieving reduction or alignment of the fractured bone or bones; the other technique consists on making a manual angle on the site of fracture and pushing with the fingers the distal fragment pulling it until the edges of the fracture enter in contact and eliminating angle thus achieving reduction, then a plaster mold is placed to keep the achieved reduction for a period from 4-6 weeks.

In the case of wrist closed fractures in adults, treatment is conservative in 75% to 80% of the cases, that is, without the need of surgery, only treatment under anesthesia and closed reduction by placing a plaster mold during approximately 6 weeks or placing of external fixators that consist on a rigid bar, generally made out of steel, to which some pins are joined by means of some dies crossing the fractured bones of patient and such fixators will keep the reduction of fracture until it becomes consolidated.

As shown in the state-of-the-art in publications number EPO248138(A1) dated 1987 Dec. 9 and U.S. Pat. No. 7,479,142(B2 dated 2009 Jan. 20.

DESCRIPTION OF TECHNICAL PROBLEM

Problem arises when despite treatment under anesthesia suitable reduction is not achieved due to the seriousness of the fracture or due to an important edema of the limb (or due to a combination of both, seriousness of fracture and important edema of the limb) that limits or complicates a lot the treatments of closed reduction; therefore, surgery is applicable to achieve suitable reduction with the implied risks thereof (anaesthetic, bleeding, longer recovery period, higher risk of articular rigidity, among others). It is worth highlighting that that in our socio-cultural environment, it is very frequent and mainly in children and in the rural environment that parents of the child visit a traditional healer or empiric healer to treat the fracture and this complicates the situation even more, because the techniques applied by such persons only hurt the tissue even more and they produce more edema with the problems that this implies, difficulty for reduction with closed technique and 95% to 100% end up with surgery to treat the fracture.

TECHNICAL SOLUTION

Invention of an apparatus was conceived to improve the closed reduction technique, mainly in complicated cases with important edema in the limb or seriousness of fracture, that generally end up with a surgical treatment due to the impossibility to achieve suitable closed reduction, that makes the closed reduction in all cases of ulna and radius possible both in the forearm and in the wrist (mainly in difficult cases, thus preventing thereby to subject patient to surgery and to all above-described inconveniences and risks of a surgery), an apparatus to reduce closed fractures of ulna and radius both in forearm and in wrist of children and wrist fractures in adults.

Since most of diaphyseal fractures (⅓ half) of ulna and radius in adults, 95%-100% are subject to surgical treatment, reduction apparatus intended to be claimed by this application does not consider these fractures.

BRIEF DESCRIPTION OF THE DRAWINGS

FIG. 1. Column (No. 1), which is a rod preferably square ¼ inch thick and 30 cm long, angled at 120 degrees by half, one of the ends of the rod is end A and the other, end B. There is another angle inverse to the above angle at 30 degrees 8 cm from end A (contrary to clockwise sense), in the apex of the second angle a rod (No. 1a) is joined, preferably round ¼ inch thick and 9 cm long that forms an angle with the rod of the 2nd. 60 degrees angle in inverse sense to this one (namely, clockwise sense) and this is end A', a rod (No. 1b) preferably square ¼ inch thick and 11 cm long is perpendicularly joined to this round rod and 4 cm from the end, round 4 mm diameter by 2 mm depth small slots or little wells (No. 1c) are made on the external face and along the square rod (1) and at a distance between one slot and the other of 1 mm followed one from the other; these slots or little wells will be made on the upper face of the rod (1b) and they are used for the entrance of the tip of a small screw (No. 3d, 5f, 6c, 7b); two circular rods ¼ inch thick and 15 cm long (No. 1d) are joined in end A of rod, joint of these rods will be perpendicular to rod (1) and in the middle of these 2 round rods, two rods (1d) will be parallel between each other, with 2.5 cm distance between them; another round rod ¼ inch thick and 19 cm long (No. 1e) is joint to end A' in the middle, perpendicular to rod (1a) and parallel to rod (1b) forming end A'. End B is the final and opposite part of rod (1) to ends A and A'.

FIG. 3. Arrow, a rod (No. 2), preferably square ⅜ inch thick and 24 cm long, a round rod (No. 2a) ¼ inch thick and 16 cm long is perpendicularly joined to an end, joined by the middle with which a "T" is formed, there is a polyethylene cover (No. 2b) 1 cmx1 cmx1 cm on the other end of rod (2), in one of its faces of the joint with rod (2a) and rod (2) becomes 1 mm thinner in 20 cm long, every .5 cm and this decrease of thickness will disappear until reaching a normal thickness of rod (2) in such a way this face becomes serrated (No. 2c), every .5 cm and with a 1 mm teeth depth x 5 mm width, these teeth (2c) are oriented towards end (2b) with polyethylene towards the end where rod (2a) is joined.

FIG. 4. The ratchet system and positioner of arrow; it is a rectangular stainless steel 2 cmx3 cm die and a square light ⅜ inch on the side (No. 3a), another rectangular die (No. 3b) is perpendicularly joined to this die and by the middle of its lower part of 1.3 cmx2.5 cm and a square light ¼ inch on the side (No. 3c), on one of the ends of this latter die there is a screw (No. 3d), 3.16 cmx3 cm long with a butterfly head to turn it, rod (2) enters into the bigger die with teeth upwards, there is a roof (No. 3e) 1.5 cmx1 cm by the middle of the die and there is a part without roof in the die as a 5 mmx1 cm window (No. 3f) and this is covered by a steel plate (No. 3g) 2.5 cmx8 mm, articulated with the roof at 1.5 cm, with an axis (No. 3h) that makes the plate entering and coming out by the window, having the window on the opposite end and a spring 1 cmx3 mm diameter (No. 3i) placed on the roof that pushes the end of the plate to towards the window (3f), where the serrated face of rod (2c) is located, and this will enable sliding of rod only in one direction (ratchet system) towards the end with polyethylene (2b), and to release or make rod (2) to slide inside the die (3), end of plate (3g) has to be pressed in the opposite direction where the spring is located (3i), finally all the system is assembled by means of the lower die (3b) to the rod (1b) that perpendicularly joined to rod (1), where it may slide throughout the length of this rod (1b), as necessary and it may be fixed with the screw (3d) that enters into the little wells or slots (1c) and fix it in the intended position.

FIG. 5. Support of forearm; it is a stainless steel 20 cm long x 4.5 cm width x 1.5 cm thick plate, angled at 90 degrees by the middle of its length, there are holes 9 mm diameter (No. 4a) on both walls, aligned in pairs, with a distance between the pair of holes of 2.5 cm and a separation between each pair of holes of 6 mm, there are 3 pairs of holes on one wall and on only 1 pair of holes on the other wall, two rods (1d) placed on the end A of column (1) enter through these holes and it is used to fix the forearm with the intended angled of the site of the fracture.

FIG. 6. Basic support point to angle the site of fracture (No. 5), it is a round rod ¼ inch thick and 9 cm long, joint on an end to a die (No. 5a) 1 cmx1 cm, with a light of ¼ inch, on the opposite end of joint with rod (5), it has a hole for entry of a screw (5f) 3/16 and 2 cm long with butterfly head to screw it down on the little wells (No. 1c) of column (No. 1); rod (5) is joined to an industrial plastic plate (No. 5b) 5 cm widthx8 cm long and 3 mm thick through a tunnel (No. 5c) of 5 mm light and at 2 cm of one of the ends of the plate and with a wall 3 mm thick and 8.3 mm long where rod (5) enters, having an end (No. 5d) of steel on the end of the rod so that such plate does not come out of the rod (5) and it may turn around itself, a polyethylene pad (No. 5e) 1 cm thick is stick on the plane side of the plate (5b) and the same measurements of the plate (5b), 8.2 cm x 5 cm.

FIG. 8. Support part of the hand or wrist and the secondary part for angle of the site of fracture (No. 6); it is a ¼ inch thick rod preferably square 10 cm long, with slots or little wells (No. 6a), 3 mmx2 mm depth in one of its faces and throughout its length, it is joined on one side to a die (No. 6b) 1 cmx1.5 cm with a ¼ inch light, its side face has a hole where a screw (No. 6c) enters 3/16x2 cm long with a butterfly head to screw it, screw will be on the face of rod (6), where the little wells (6a) are located, a round rod (No. 6d) ¼ inch thick is joined on the opposite side of the die in angle with rod (6) 90 degrees, length of round rod is 9 cm, round rod (6d) enters into a roller (6e), a polyethylene plastic 3 mm thick (No. 6f) is stick all around its external circumference and length, such roller will spin around the rod (6d), a die (No. 6g) 1.3 cmx1.3 cm with a ¼ inch light is joined to the end of rod (6d) and a hole in the lower face of the die where a screw (No. 6h) 3/16x2 cm long with butterfly head enters to be screwed.

FIG. 9. Support of the hand or forearm (No.7); it is a round rod ¼ inch and 9 cm long, it is joined to a square die (No. 7a) 1 cmx1.5 cm with a ¼ inch light on one of its ends, that in the opposite end to the joint of rod (7), the die (7a) will have a hole wherein a screw will enter (No. 7b), 3/16x1.5 cm long with butterfly head to be able to screw it, it will have an industrial plastic roller (No. 7c) 3 mm thick and a 5 mm light throughout the length of the round rod, the external face of roller (7c) is covered by polyethylene 3 mm thick (No. 7d), there is an end (7e) at the end of rod (7) opposite to die (7a) preventing the roller (7c) from coming out of the rod (7) but it will allow that such roller (7c) turns around the rod (7c).

FIG. 11. Support of the end on the necessary site (No. 9)), a square rod ¼ inch thick and 5 cm long, with little wells (No. 9a) 3 mm diamgerx2depth on the upper face and throughout the length, a square plate (No. 9b) 2.5 cm side and 2 mm thick will be joined to an end, joined by the middle of one of its sides and on the end, a polyethylene (No. 9c) 3 mm thick covering its complete area is stick on the opposite face of the joint plate of rod (9).

DESCRIPTION OF THE INVENTION

Characteristic details of this novel apparatus are clearly shown in the following description and in the drawings enclosed hereto and an illustration thereof following the same reference signs to indicate the parts and the figures shown.

Figure 13:
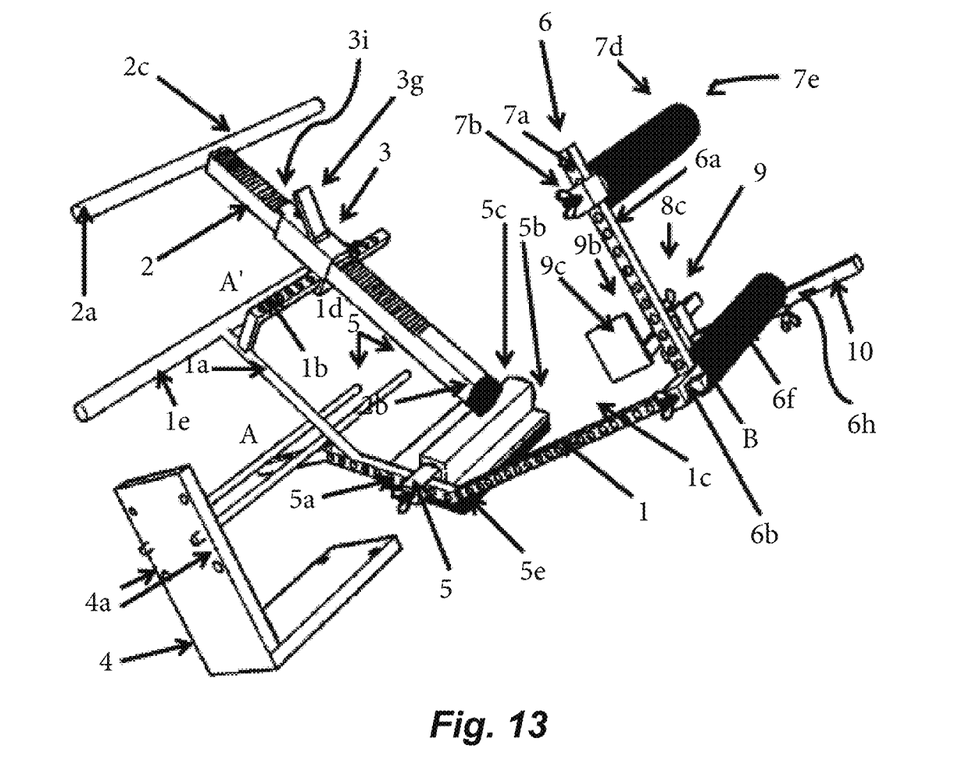
FIG. 13. Apparatus already assembled with all its parts, according to one embodiment.
Figure 14:
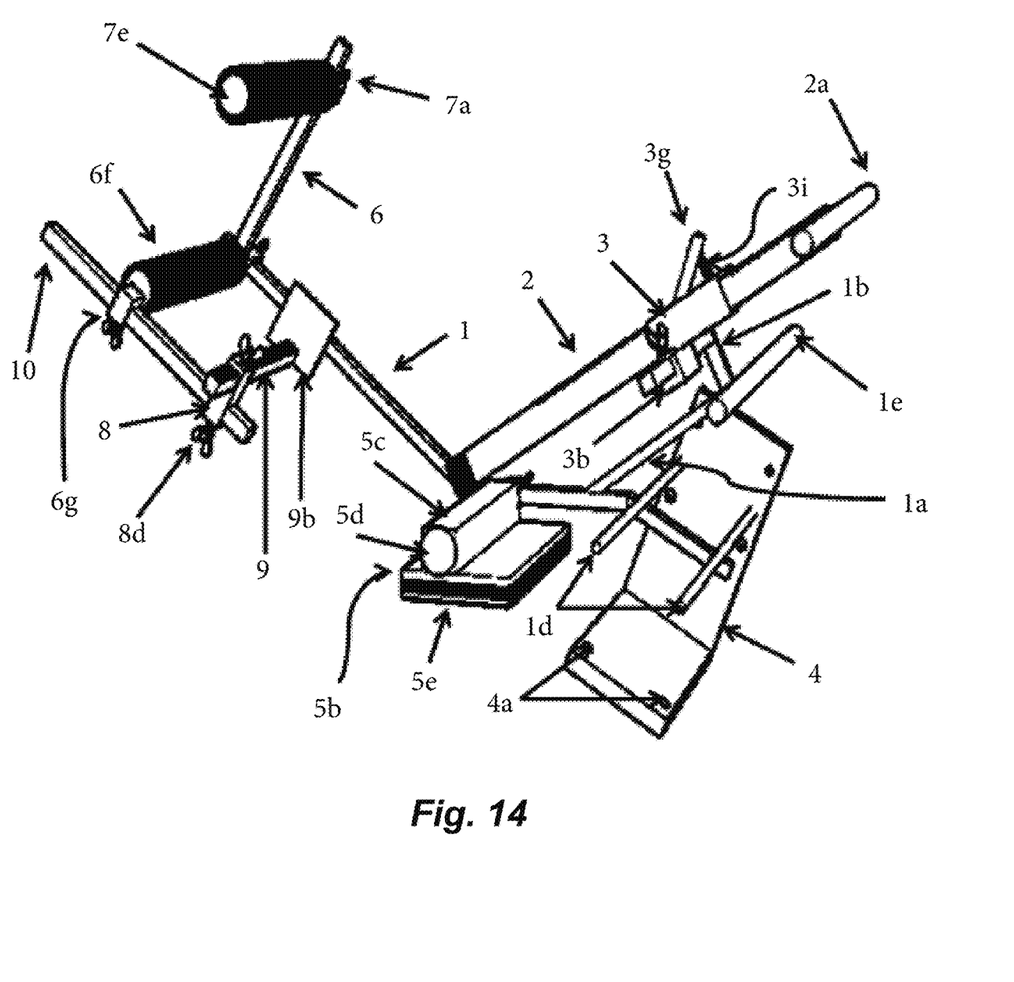
FIG. 14. Apparatus already assembled with all its parts, according to one embodiment.

It is an apparatus comprised of 10 parts, each one of them with sub-parts. All rods are preferably made out of stainless steel and all joints of rods are preferably welded but they may also be made out of titanium, aluminum, plastic or any useful material; FIGS. 13 and 14 show the apparatus already assembled.

Figure 1:
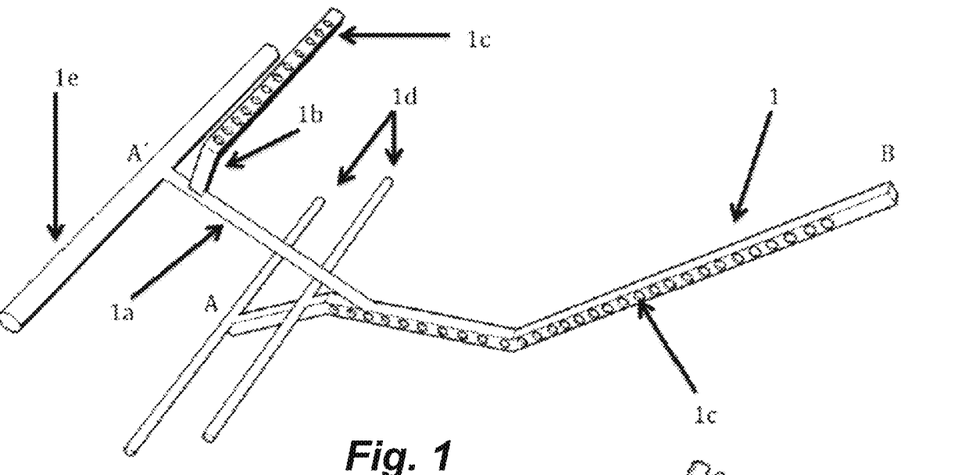
Figure 2:
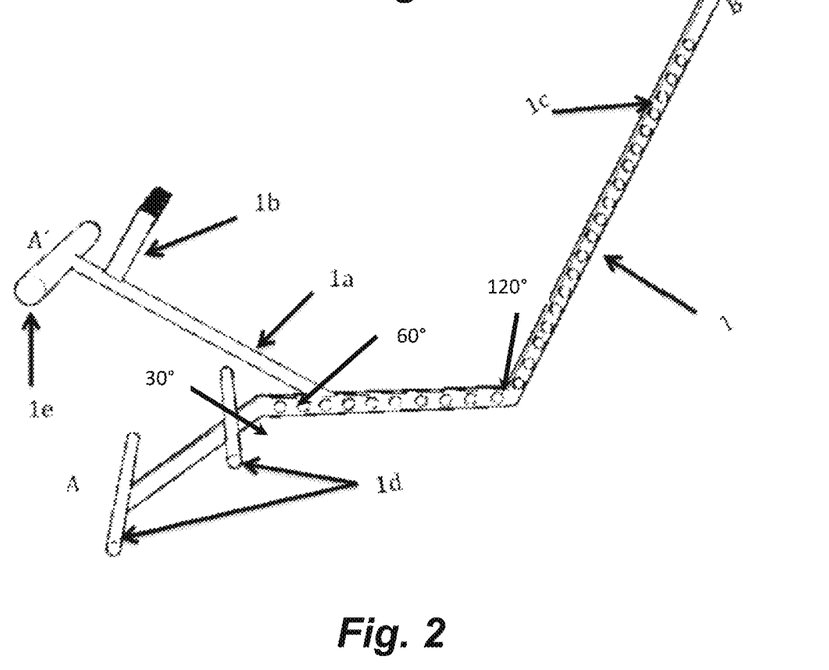
FIG. 2. An exemplary view of an apparatus, according to one embodiment.

Column (No. 1) is observed in FIGS. 1 and 2. It is a rod preferably square ¼ inch thick and 30 cm long, angled at 120 degrees by half, one of the ends of the rod is end A and the other, end B; there is another angle inverse to the above angle at 30 degrees 8 cm from end A (contrary to clockwise sense), in the apex of the second angle a rod (No. 1a) is joined, preferably round ¼ inch thick and 9 cm long that forms an angle with the rod of the $2^{nd}$ 60 degrees angle in inverse sense to this one (namely, clockwise sense) and this is end A', a rod (No. 1b) preferably square ¼ inch thick and 11 cm long is perpendicularly joined to this round rod and 4 cm from the end, round 4 mm diameter by 2 mm depth small slots or little wells (No. 1c) are made on the external face and along the square rod (1) and at a distance between one slot and the other of 1 mm followed one from the other; these slots or little wells will be made on the upper face of the rod (1b) and they are used for the entrance of the tip of a small screw (No. 3d, 5f, 6c, 7b); two circular rods ¼ inch thick and 15 cm long (No. 1d) are joined in end A of rod, joint of these rods will be perpendicular to rod (1) and in the middle of these 2 round rods, two rods (1d) will be parallel between each other, with 2.5 cm distance between them; another round ¼ inch thick and 19 cm long (No. 1e) is joint to end A' in the middle, perpendicular to rod (1a) and parallel to rod (1b) forming end A', as shown in FIGS. 1 and 2. End B is the final and opposite part of rod (1) to ends A and A'.

Figure 3:
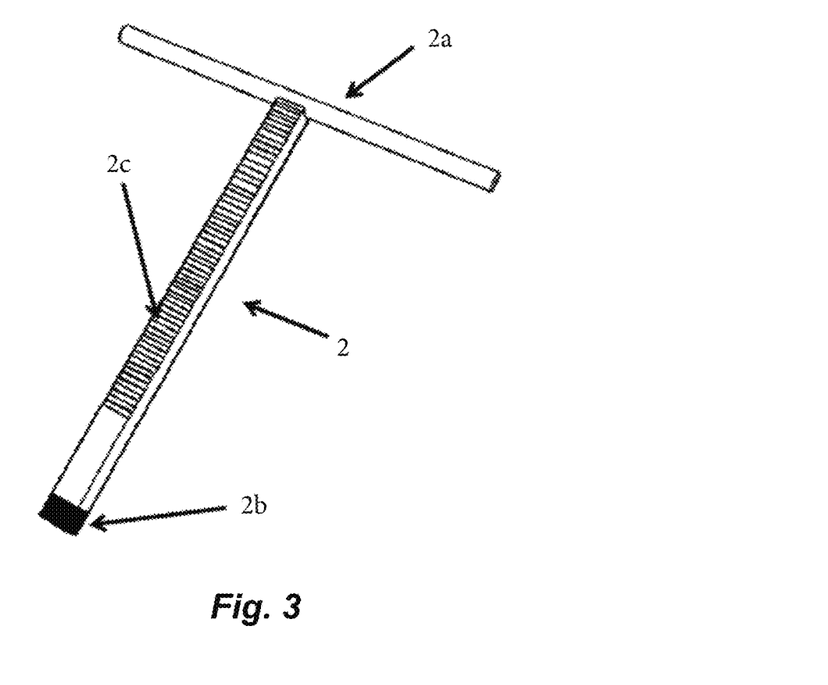

The arrow, a rod (No. 2), is observed in FIG. 3, preferably square ⅜ inch thick and 24 cm long, a round rod (No. 2a) ¼ inch thick and 16 cm long is perpendicularly joined to an end, joined by the middle with which a "T" is formed, there is a polyethylene cover (No. 2b) 1 cm×1 cm×1 cm on the other end of rod (2), in one of its faces of the joint with rod (2a) and rod (2) becomes 1 mm thinner in 20 cm long, every 0.5 cm and this decrease of thickness will disappear until reaching a normal thickness of rod (2) in such a way this face becomes serrated (No. 2c), every 0.5 cm and with a 1 mm teeth depth×5 mm width, these teeth (2c) are oriented towards end (2b) with polyethylene towards the end where rod (2a) is joined.

Figure 4:
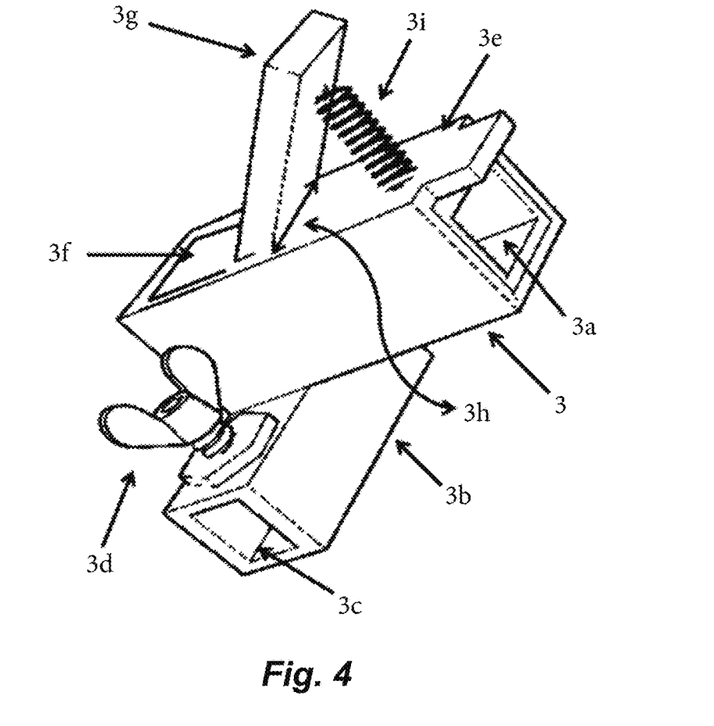

Ratchet system and positioner of arrow (No. 3) are observed in FIG. 4, it is a rectangular stainless steel 2 cm×3 cm die and a square light ⅜ inch on the side (No. 3a), another rectangular die (No. 3b) is perpendicularly joined to this die and by the middle of its lower part of 1.3 cm×2.5 cm and a square light ¼ inch on the side (No. 3c), on one of the ends of this latter die there is a screw (No. 3d), 3.16 cm×3 cm long with a butterfly head to turn it, rod (2) enters into the bigger die with teeth upwards, there is a roof (No. 3e) 1.5 cm×1 cm by the middle of the die and there is a part without roof in the die as a 5 mm×1 cm window (No. 3f) and this is covered by a steel plate (No. 3g) 2.5 cm×8 mm, articulated with the roof at 1.5 cm, with an axis (No. 3h) that makes the plate entering and coming out by the window, having the window on the opposite end and a spring 1 cm×3 mm diameter (No. 3i) placed on the roof that pushes the end of the plate to towards the window (3f), where the serrated face of rod (2c) is located, and this will enable sliding of rod only in one direction (ratchet system) towards the end with polyethylene (2b), and to release or make rod (2) to slide inside the die (3), end of plate (3g) has to be pressed in the opposite direction where the spring is located (3i), finally all the system is assembled by means of the lower die (3b) to the rod (1b) that perpendicularly joined to rod (1), where it may slide throughout the length of this rod (1b), as necessary and it may be fixed with the screw (3d) that enters into the little wells or slots (1c) and fix it in the intended position.

Figure 5:
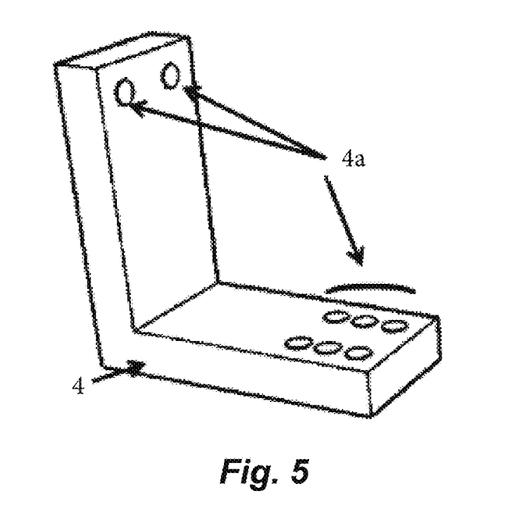

Support of forearm (No. 4) may be seen in FIG. 5, it is a stainless steel 20 cm long×4.5 cm width×1.5 cm thick plate, angled at 90 degrees by the middle of its length, there are holes 9 mm diameter (No. 4a) on both walls, aligned in pairs, with a distance between the pair of holes of 2.5 cm and a separation between each pair of holes of 6 mm, there are 3 pairs of holes on one wall and on only 1 pair of holes on the other wall, two rods (1d) placed on the end A of column (1) enter through these holes and it is used to fix the forearm with the intended angled of the site of the fracture.

Figure 6:
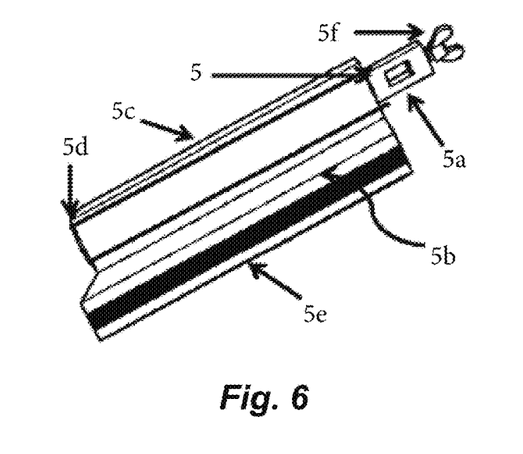
Figure 7:
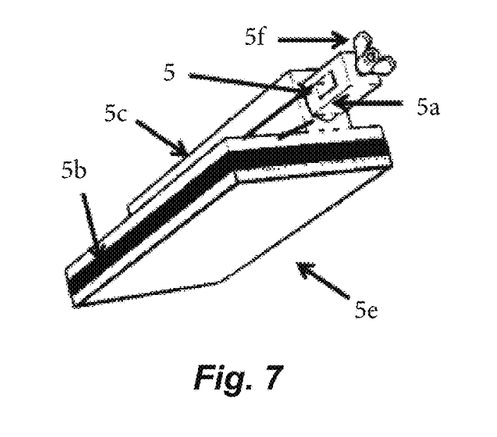
FIG. 7. An exemplary view of an apparatus, according to one embodiment.

Basic support point is observed in FIGS. 6 and 7 to angle the site of fracture (No. 5), it is a round rod ¼ inch thick and 9 cm long, joint on an end to a die (No. 5a) 1 cm×1 cm, with a light of ¼ inch, on the opposite end of joint with rod (5), it has a hole for entry of a screw (5f) 3/16 and 2 cm long with butterfly head to screw it down on the little wells (No. 1c) of column (No. 1); rod (5) is joined to an industrial plastic plate (No. 5b) 5 cm width×8 cm long and 3 mm thick through a tunnel (No. 5c) of 5 mm light and at 2 cm of one of the ends of the plate and with a wall 3 mm thick and 8.3 mm long where rod (5) enters, having an end (No. 5d) of steel on the end of the rod so that such plate does not come out of the rod (5) and it may turn around itself, a polyethylene pad (No. 5e) 1 cm thick is stick on the plane side of the plate (5b) and the same measurements of the plate (5b), 8.2 cm×5 cm.

Figure 8:
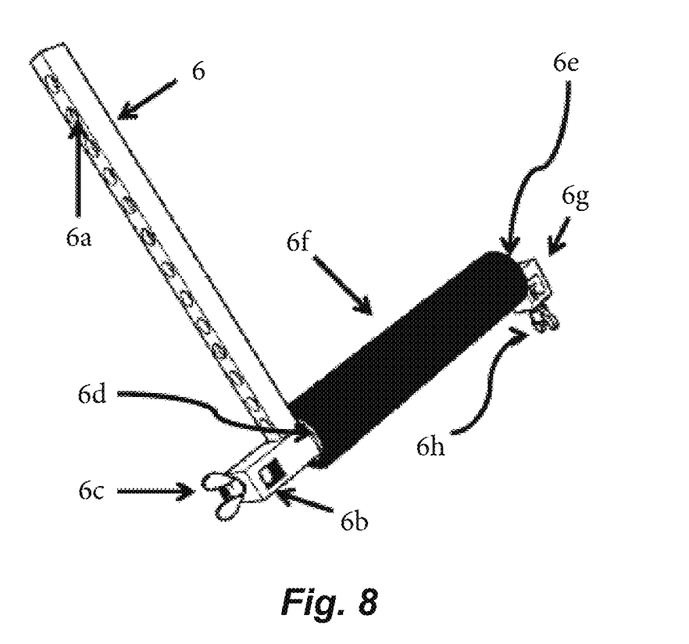

Support part of the hand or wrist and the secondary support part for angle of the site of fracture (No. 6) is observed in FIG. 8, that is a ¼ inch thick rod preferably square 10 cm long, with slots or little wells (No. 6*a*), 3 mm×2 mm depth in one of its faces and throughout its length, it is joined on one side to a die (No. 6*b*) 1 cm×1.5 cm with a ¼ inch light, its side face has a hole where a screw (No. 6*c*) enters 3/16×2 cm long with a butterfly head to screw it, screw will be on the face of rod (6), where the little wells (6*a*) are located, a round rod (No. 6*d*) ¼ inch thick is joined on the opposite side of the die in angle with rod (6) 90 degrees, length of round rod is 9 cm, round rod (6*d*) enters into a roller (6*e*), a polyethylene plastic 3 mm thick (No. 6*f*) is stick all around its external circumference and length, such roller will spin around the rod (6*d*), a die (No. 6*g*) 1.3 cm×1.3 cm with a ¼ inch light is joined to the end of rod (6*d*) and a hole in the lower face of the die where a screw (No. 6*h*) 3/16×2 cm long with butterfly head enters to be screwed.

Figure 9:
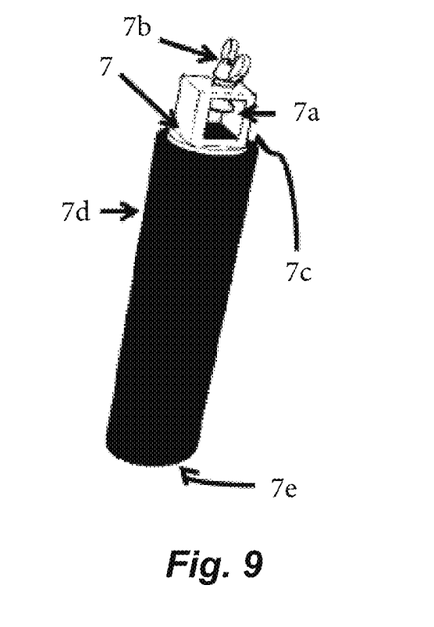

Support of the hand or forearm (No. 7) is observed in FIG. 9, it is a round rod ¼ inch and 9 cm long, it is joined to a square die (No. 7*a*) 1 cm×1.5 cm with a ¼ inch light on one of its ends, that in the opposite end to the joint of rod (7), the die (7*a*) will have a hole wherein a screw will enter (No. 7*b*), 3/16×1.5 cm long with butterfly head to be able to screw it, it will have an industrial plastic roller (No. 7*c*) 3 mm thick and a 5 mm light throughout the length of the round rod, the external face of roller (7*c*) is covered by polyethylene 3 mm thick (No. 7*d*), there is an end (7*e*) at the end of rod (7) opposite to die (7*a*) preventing the roller (7*c*) from coming out of the rod (7) but it will allow that such roller (7*c*) turns around the rod (7*c*).

Figure 10:
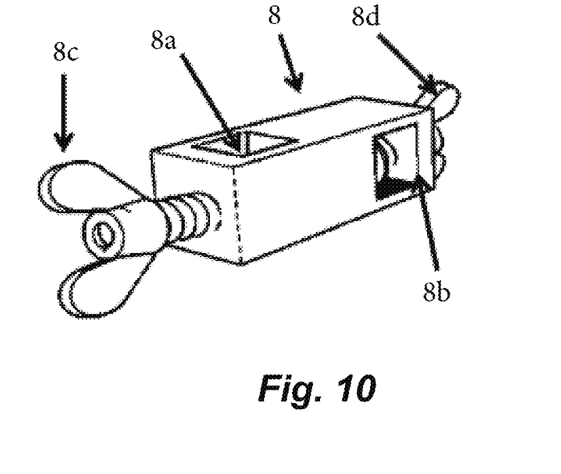
FIG. 10. Part 8 (No. 8); a rectangular cylinder 3 cmx1. 3 cmx1.3 cm with double light (No. 8a and 8b) ¼ inch each one, and perpendicular between each other, and a wall separating both 5 mm lights, there is a hole on both ends of the cylinder where a screw enters in each hole (No. 8c and 8d) 3/16x1.5 long with butterfly head to screw it, both screws will enter in the light of each end, this will fix two rods (9) and (10) that perpendicularly one from the other enter by both lights.

FIG. 10 shows part 8 (No. 8), a rectangular cylinder 3 cm×1.3 cm×1.3 cm with double light (No. 8*a* and 8*b*) ¼ inch each one, and perpendicular between each other, and a wall separating both 5 mm lights, there is a hole on both ends of the cylinder where a screw enters in each hole (No. 8*c* and 8*d*) 3/16×1.5 long with butterfly head to screw it, both screws will enter in the light of each end, this will fix two rods (9) and (10) that perpendicularly one from the other enter by both lights.

Figure 11:
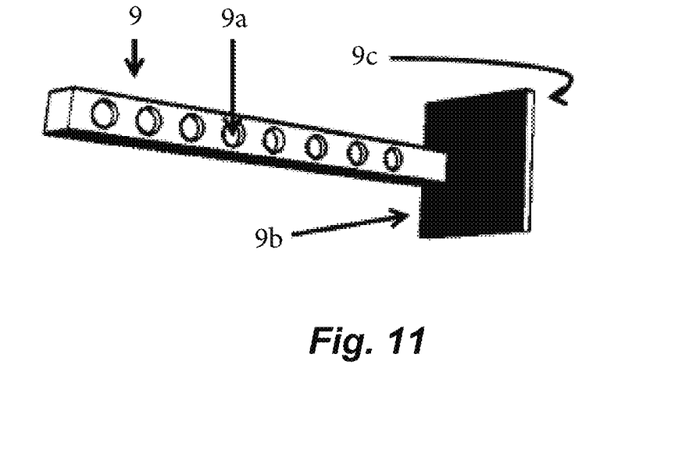

FIG. 11 shows the support of the end on the necessary site (No. 9), a square rod ¼ inch thick and 5 cm long, with little wells (No. 9*a*) 3 mm diamger×2 depth on the upper face and throughout the length, a square plate (No. 9*b*) 2.5 cm side and 2 mm thick will be joined to an end, joined by the middle of one of its sides and on the end, a polyethylene (No. 9*c*) 3 mm thick covering its complete area is stick on the opposite face of the joint plate of rod (9).

Figure 12:
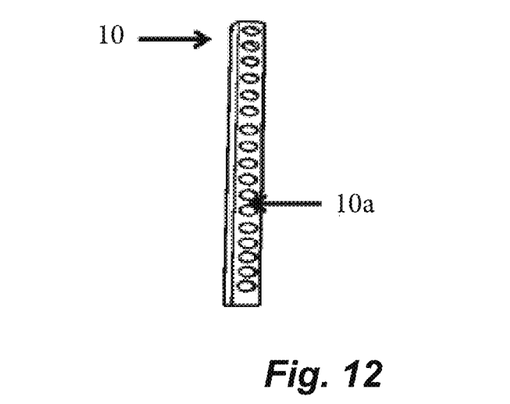
FIG. 12. Part 10 (No. 10) a square rod ¼ inch thick and 5 cm long with little wells or slots (No. 10a) 3 mm diameterx2 mm depth in one of its faces and throughout its length, this piece is assembled on one side with part (8) and on the other with part (6g) and it is fixed with both parts with screws (8c) and (6h) of both pieces as necessary as shown in FIGS. 13 and 14.

FIG. 12 shows part 10 (No. 10), a square rod ¼ inch thick and 5 cm long with little wells or slots (No. 10*a*) 3 mm diameter×2 mm depth in one of its faces and throughout its length, this piece is assembled on one side with part (8) and on the other with part (6*g*) and it is fixed with both parts with screws (8*c*) and (6*h*) of both pieces as necessary as shown in FIGS. 13 and 14.

FIGS. 13 and 14 show the apparatus already assembled with all its parts.

As this type of fractures occur when patient falls and puts ahead the hand with the wrist in extension to prevent hurting himself/herself, and all impact is absorbed by the wrist and the forearm, fragments of fracture are displaced, and the distal fragment rides on the rear part of the proximal fragment; therefore, the site of the fracture will present certain degree of dorsal angle with the characteristic "dinner fork deformity".

The way in which this apparatus will work is as follows:

First thing to be done is to increase the deformity or the angle of the limb (wrist or forearm) dorsally on the site of 60-70 degrees fracture, then pressure is exerted on the distal fragment of the fracture to distally push it until moving the distal fragment and have it contact the proximal fragment right where the fracture is located, once the above is achieved and both fragments of fracture in contact by the rear cortical of both fragments end-terminal, angle with which we started the process is eliminated taking the wrist towards flexion and the arrow used as post and it pushes the distal fragment to its position, thus achieving reduction. Therefore, the first thing is adjusting on custom basis the apparatus, this depends on the fractured part to be reduced, either wrist or forearm, since depending on the size of the limb to be treated, all parts of the apparatus are adjusted, for example, parts 5 and are assembled to part 1 and they are placed on the suitable position and they are fixed with screws, (5*f*), (6*e*) that enter into the little wells or slots (1*c*) and that guarantees that it position is tightly held, part 7 is adjusted to part 6 on the same form than parts 5 and 6 with the difference that parts 5 and 6 are joined with part 1 and part 7 is joined with part 6, as shown by FIGS. 13 and 14, part 3 is adjusted depending on the direction of the arrow, that is the site where the distal fragment of the fracture will be pushed and if the fractured limb is right it necessarily moves towards the left of the rod (1*b*) where part 3 slides and if the fractured limb is left it necessarily moves towards right and where part 3 needs to be left, it is fixed with screw (3*d*) which tip enters into the slot or little well (1*c*) of the rod (1*b*) with which it is assembled, part 8 is joined to part 10 and part 9 to keep wrist fixed or forearm in the necessary position to reduce the fracture, as shown by FIGS. 13 and 14, once the apparatus is individually adjusted to the affected wrist of forearm, limb is placed in parallel on part 1, the hand or wrist is placed over the roller (6*e*) of part 6 and under plate (5*b*) of part 5, part 7 is adjusted to hold the hand or wrist between the two rollers (6*e*) and (7*c*) of parts 6 and 7 and since these two rollers spin they allow mobility of the hand or wrist upon angle of the fracture, and this is made upon exerting pressure on end A' of part 1, that supporting on the forearm on the dorsal part with the plate of part 5, taking the back of the hand or wrist to an angle of up to 60 or 70 degrees, once the above is achieved, the arrow (2) is pushed with both hands exerting pressure on the end of part (2*a*), on the round rod joined to the arrow making a T and supporting the fingers of both hands on round rod (1*e*) joined to the end A' of part 1, both round rods (1*e*) (2*a*) of part 2 are parallel and as in part 1, in such a way that upon tightening both rods with both hands, arrow (2) slides in the die (3) of piece 3 which rash system will only allow sliding of arrow in a single direction and in each advance of the arrow and jump of the serrated part (2*c*) of the arrow, it will correspond to half centimeter and a click will be heard (each click will be denominated a shot) which purpose is to push the distal fragment of the fractured bone, with the necessary shots as applicable until having both fractured fragments in contact by the dorsal cortical of both fragments and then angle to which the affected limb was originally taken is eliminated, taking the wrist to flexion and upon eliminating such angle taking it to 0 degrees, intended reduction of the fracture is achieved; then, the apparatus is removed without losing the achieved correction and a circular plaster apparatus is placed on the necessary position to keep correction of the fracture until consolidation of the fracture has been completed.

The above is verified with the X-rays after the reduction, seriated in the monitoring of patient.

The design and form in which this apparatus works is the novel aspect of the apparatus, since it allows solving one of the most frequent problems in orthopaedics and traumatology such as wrist fractures in children and adults and ulna and radius fractures in children that as it may be seen in the prevalence and frequency statistics are quite frequent as above-stated that are treated without problems with the conventional techniques when they are recent fractures, namely one or 2 hours evolution but when the time of evolution exceeds 24 hours, the resulting edema makes very difficult the reduction of the fracture with a closed technique, and the difficulty is directly proportional to the evolution time and/or edema of the limb and in several occasions in view the impossibility of achieving reduction with a closed technique, the open technique (surgery) must be used with all the implied risks therefrom, such as anesthesia, bleeding, infection, recovery period and recovery.

This apparatus may reduce both fractures of less than 30 minutes evolution and those exceeding 24 or 48 hours evolution or those previously manipulated by empiric or traditional healers that far from reducing the fracture, they hurt even more the tissues and caused more edema, thus making the treatment of such fractures with closed technique difficult.

I claim:

1. An apparatus for the manipulation and reduction or alignment of closed fractures of the wrist or forearm bones comprising:

a column (1) made of a stainless steel square rod ¼ inch (0.0635 cm) thick and 30 cm in length having an A end and a B end, the column comprising a double angle including a first angle positioned at half of a length of the column (1) and at 120 degrees, and a second angle of 30 degrees positioned at 8 cm from the A end and opposite to the first angle, a round rod (1a) of ¼ inch (0.635 cm) diameter is attached to and in 9 cm in length welded at one end in a vertex of the second angle, forming a 60° angle with the square rod of the second angle clockwise, a second end of the welded rod is an A' end with the column (1) being the backbone of the apparatus;

wherein the column (1) comprises notches or pits (1c) having a diameter of 4 mm and a depth of 2 mm on a side face and throughout a length of the column (1) and perpendicularly attached to other 2 rods (1d) parallel to each other and of ¼ inch (0.635 cm) diameter round in the A end and in an A' end that is perpendicularly attached and with one rod (1e) of ¼ inch (0.635 cm) of round diameter, forming a T with the A end;

wherein a double rectangular die (3) (3b) with double square light perpendicular to each other assembled to one of the dies (3b) with the square rod (1b) of ¼ inch (0.635 cm) thickness and 11 cm in length, having in a top face notches or pits of the same dimensions of the column (1), said square rod (1b) attached to the round rod (1a) at the A' end and the die (3) receives another square rod of ⅜ inch (0.9525 cm) thickness and T-shaped toothed, which together form a ratchet system allowing advancement of a side of T-shaped rod (2) within the die (3) in only one direction by converting said T-shaped rod (2) in an arrow that moves forward from a half centimeter to a half centimeter which is the distance of each tooth or steps having in each face and its entire length, in an end of said side (3b) there is a screw (3d), said die (3b) may slide along the square rod (1b) and be fixed introducing the screw (3d) in a notch or pits of the square rod (1b);

wherein a forearm fastener (4) which a 20 cm sheet length by 4.5 cm width and 1.5 cm thickness bent by half at 90 degrees and with 8-hole pairs (4a) to assembly with the rods (1d) parallel of the A end;

wherein a primary fulcrum to angle the fracture (5) comprises a rectangular platform of 5 cm by 8 cm by 3 mm thickness (5b) of industrial plastic comprising polyethylene (5e) in a lower surface of one of a rectangular faces of 1 cm thickness and on an opposite side by means of a tunnel (5c) of 5 mm diameter is attached a rod (5), said rod (5) is attached to a central face of the column (1) by a square die (5a) by which the rod is introduced and perpendicular therefrom, being fixed to the column by a screw (5f) of 3/16 inch (0.47625 cm) of diameter passing through connecting die (5a) and the screw (5f) is introduced on the notches or pits (1c) of the side face of the column;

wherein a secondary fulcrum to angle is a square rod (6) of 0.635 cm thickness with notches or pits (6a) on both of its faces and attached to round rod (6d) made of stainless steel of ¼ inch (0.635 cm) of diameter and 9 cm length with which comprises a 90 degree angle, which are assembled to square die (6b) located at a vertex and with a square light of ¼ inch (0.635 cm) thickness by which the column (1) is introduced and with a screw (6c) of 3/16 inch (0.47625 cm) of diameter introducing the square die and is introduced on the notches or pits (1c) of the side face of the column (1), the rod (6d) is introduced in the rod (6e), which is an industrial plastic and on its outside face is covered with a polyethylene plastic (6f) 3 mm thick and throughout its length, allowing a roller to rotate on the rod (1d) (6d);

wherein a fulcrum for correcting the angle is another rod (7c) of the same materials of the secondary fulcrum, assembled to a round rod (7) of stainless steel of 0.635 cm diameter and 9 cm length, the round rod (7) is joined to the square rod (6) of the secondary fulcrum through a square die (7a) with a square light ¼ light of 0.635 thickness by which the square rod (6) in introduced and fixed with a screw (7b) 3/16 inch (0.47625 cm) passing the die and is introduced on the notches or pits (6a) of the square rod (6);

wherein the hand fastener is a square stainless steel rod (9) of 0.635 cm thickness and of 5 cm length with notches or pits (9a) on an upper side and throughout its length, and on one end is attached welded to a stainless steel sheet (9b) of 2.5 cm sides and 2 mm thickness and on an opposite face of the stainless steal sheet is adhered polyethylene (9c) of 3 mm thickness; and wherein a stainless steel die (8) with double square light (8a) (8b) of 0.635 cm thickness and perpendicular to each other (8a) and receives the rod (9) of the hand fastener and the other light (8b) receives stainless steel rod (10) of ¼ inch (0.635 cm) thickness of 5 cm length and with notches or pits (10a) on one face and throughout its length on each end (8) there is a hole wherein screws are introduced (8c, 8d), said screws (8c, 8d) are introduced in a notch or pit (9a, 10a) of the rod (9) of the hand fastener and of the square rod (10) to be fixed, the square rod (10) is also assembled to die (6g) located in an end of round rod (6d) containing the roller (6e) used that works as the secondary fulcrum or rest of the hand or the forearm of patient, said die (6g) having a hole in a lower face wherein a screw (6h) is introduced, said screw (6*h*) is introduced on the notch or pit (10*a*) of the square rod (10) to fix it in place.

\* \* \* \* \*

UNITED STATES PATENT AND TRADEMARK OFFICE
CERTIFICATE OF CORRECTION

| | |
|---|---|
| PATENT NO. | : 12,171,684 B2 |
| APPLICATION NO. | : 17/424997 |
| DATED | : December 24, 2024 |
| INVENTOR(S) | : Rubén Fernando Sáyago |

Page 1 of 1

It is certified that error appears in the above-identified patent and that said Letters Patent is hereby corrected as shown below:

In the Claims

• In Claim 1, at Column 10, Lines 34-35, please delete "on the rod (1d) (6d);" and insert -- on the rod (6d); -- therefor.

• In Claim 1, at Column 10, Line 51, please delete "stainless steal" and insert -- stainless steel -- therefor.

• In Claim 1, at Column 10, Lines 56-57, please delete "receives stainless steel rod" and insert -- receives the stainless steel rod -- therefor.

• In Claim 1, at Column 10, Lines 64-65, please delete "the roller (6e) used that works" and insert -- the roller (6e) that works -- therefor.

Signed and Sealed this
Fourth Day of February, 2025

Coke Morgan Stewart
*Acting Director of the United States Patent and Trademark Office*